(12) United States Patent  (10) Patent No.: US 8,808,598 B1
Meyer                      (45) Date of Patent:     Aug. 19, 2014

(54) MIFA (MOLDING IMPRESSION FABRICATION APPARATUS)

(76) Inventor: Grant C. Meyer, Muskegon, MI (US)

( * ) Notice: Subject to any disclaimer, the term of this patent is extended or adjusted under 35 U.S.C. 154(b) by 62 days.

(21) Appl. No.: 12/288,304

(22) Filed: Oct. 18, 2008

(51) Int. Cl.
B29C 33/42 (2006.01)
A61L 27/00 (2006.01)

(52) U.S. Cl.
CPC .................................. *A61L 27/00* (2013.01)
USPC ............................... 264/222; 264/220; 425/2

(58) Field of Classification Search
USPC ..................................... 425/2; 264/220, 222
See application file for complete search history.

(56) References Cited

U.S. PATENT DOCUMENTS

| | | |
|---|---|---|
| 3,995,002 A | 11/1976 | Brown |
| 4,503,576 A | 3/1985 | Brown |
| 4,522,777 A | 6/1985 | Peterson |
| 4,747,989 A | 5/1988 | Peterson |
| 4,906,425 A * | 3/1990 | Poussou ........................ 264/102 |
| 4,962,762 A | 10/1990 | Beekil |
| 5,282,328 A | 2/1994 | Peterson |
| 5,843,483 A | 12/1998 | Theriault et al. |
| 5,908,397 A | 6/1999 | Tatum et al. |
| 6,782,630 B2 | 8/2004 | Root |

\* cited by examiner

*Primary Examiner* — Galen Hauth
(74) *Attorney, Agent, or Firm* — Lanny M. Englund

(57) ABSTRACT

The present invention relates to a MIFA (Molding Impression Fabrication Apparatus) providing the practitioner a quick and accurate means to create an orthotic impression of a patients foot, leg, arm, and torso. Both traditional and intrinsic biomechanical correction modifications, may be incorporated as well. The patient can be placed back into the MIFA impression for immediate feedback of the modifications and changes. MIFA may also be utilized for direct forming to fabricate an orthosis directly to the patient. CAD/CAM scanning can be utilized with MIFA, to both compliment and refine the negative and positive impressions obtained from MIFA.

13 Claims, 3 Drawing Sheets

MIFA (MOLDING IMPRESSION FABRICATION APPARATUS)

FIELD OF THE INVENTION

The present invention relates to MIFA (Molding Impression Fabrication Apparatus). Also, MIFA provides the practitioner a quick and accurate means to create an orthotic impression of a patient's leg, arm, or body corrected alignment with a new, novel, and state of the art process. The initial negative orthotic impression may then be easily modified for the forming of a completed positive impression. Modifying the impression may relieve normal boney prominences or painful areas of the foot, leg, or body; as well as it may be modified to redistribute forces, and to change the biomechanics of the lower extremities. The patient can then be placed back into the MIFA impression for immediate feedback of the relief or changes added. MIFA may also be utilized for direct forming to fabricate an orthosis directly to the patient. MIFA provides a useful tool for patient evaluation as with the lower extremity. By placing the patient into the corrected mold, the practitioner may determine the amount of support needed for the patient to stand independently and evaluate the changes and modifications made. The practitioner can then build a supportive system to the patient and re-modify if needed.

DESCRIPTION OF THE RELATED ART

The prior art relates generally to Custom foot beds for footwear as recited in U.S. Pat. No. 5,582,328 to Peterson and Method and Apparatus for making corrected custom molds in U.S. Pat. No. 4,522,777 and U.S. Pat. No. 4,747,989 also to Peterson with cross references to a brochure Entitled, "Conform'able SIDAS" printed by SIDAS, Grenoble, France, and as advertised by SIDAS at its Internet Website. It should be further noted that, although SIDAS is extensively advertised on the Internet at its Website, and in published marketing brochures, there are no issued patents of record to SIDAS, nor is the novel and unique MIFA process of the subject invention described by SIDAS in any fair combination in its Website and/or marketing brochures.

U.S. Pat. No. 6,782,630 to Root describes a device and method for use in taking molds of feet but does not teach or claim the MIFA subject invention. U.S. Pat. No. 5,908,397 to Tatum et al teaches and describes a device for positioning and supporting legs during casting including a pair of foot positioning supports and sole plates and a rigid elongated center frame rail. Tatum et al does not claim or teach the subject MIFA invention.

U.S. Pat. No. 5,843,483 to Theriault et al relates an Apparatus for forming a foot orthotic including a housing for an inflatable bladder. Theriault et al neither teaches nor describes the subject invention.

U.S. Pat. No. 4,962,762 to Beekil describes and claims a modular self-contained orthotic device for inexpensively and efficiently forming and casting and impression of the bottom portion of an individual's foot. This patent does not teach, describe, or claim the MIFA invention.

U.S. Pat. No. 4,503,576 to Brown describes and teaches a method of making an orthotic appliance for use between a foot and a shoe including steps of providing a support platform, covering the foot in an air tight bag, and inserting a vacuum conduit into the bag; however it does not describe or claim the subject invention in any fair combination.

U.S. Pat. No. 3,995,002 to Brown teaches and describes an Orthocasting System for producing a negative mold of the bottom of a foot and a method of forming a custom foot support appliance comprising the steps of applying a molding material to the sole of the foot, covering the molding material with an air tight bag secured in air tight relation to the ankle of the user, applying a vacuum to the air tight bag, casting a positive mold of the bottom of the foot, and forming a rigid foot support appliance on the positive mold. The Brown patent neither teaches, describes, or claims the subject MIFA and/or process for accurately creating an impression of a patient's leg, foot, arm, or body with corrected alignment and not just the bottom of a foot.

SUMMARY OF THE INVENTION

The present MIFA invention overcomes the limitations and disadvantages of the prior art by enabling the practitioner with a quick and accurate means to create an impression of a patient's foot, ankle, leg, or body with corrected alignment, thus providing with the MIFA process, a smoother and more durable cast than expensive CAD/CAM systems within the orthotic profession.

In the MIFA (Molding Impression Fabrication Apparatus) process, liquid plaster or similar mold forming formulas may be poured into the negative impression providing a corrected positive mold or what is otherwise considered a modified positive cast or mold. This cast can then be utilized to fabricate the patient's orthosis. Utilizing this apparatus eliminates the need of traditional casting materials such as plaster bandage or various poly wraps for impression making. The apparatus can produce a smoother and more durable cast than scanned CAD/CAM systems. Although the negative impression may be scanned to library the information of the patient, the need for expensive software and milling machines are no longer necessary. MIFA is also capable of producing the modified cast in a shorter time frame.

MIFA may also be utilized for direct forming to fabricate an orthosis directly to the patient. By placing a pliable blank consisting of a heated thermo-formable material i.e. Kydex, PVC, EVA, etc. into the patient's negative impression, and then replacing the same appendage or body area upon the formable material creating a sandwiching effect. Then essentially compressing the material between the positive and a negative thus giving a set shape to the material.

An important process step in the MIFA (Molding Impression Fabrication) process involves the use of bladders. The bladder shape is larger in size covering the anatomical portion to be molded (i.e. foot, ankle, leg, etc.). Because the bladders are so subtle, they are contained in a semi-rigid shell for controlling the placement, and attachment reservoir for the disbursement of beads, and vibration transmission of the beads. The glass beads contained in the attachment shell bladder reservoir are of sphere shaped, allowing air passage in all directions between the beads. Bladders are comprised of elastic materials such as latex, TPE, and/or a membrane or elastic subtle barrier between the beads and foot, ankle, leg, etc. Another critical and unique process step of the MIFA process is vibration transmission submitted to the glass beads within the shell bladder reservoir. This vibration transmission to the beads, allows them to move freely within the bladder. This transmission also enables the correct amount to fill the bladder from the reservoir providing the correct volume of beads between the appendage and the shell. The freedom of movement of the beads forms a detailed contour or image of the body part against the bladder.

DETAILED DESCRIPTION OF THE PREFERRED EMBODIMENT

Figure 1:
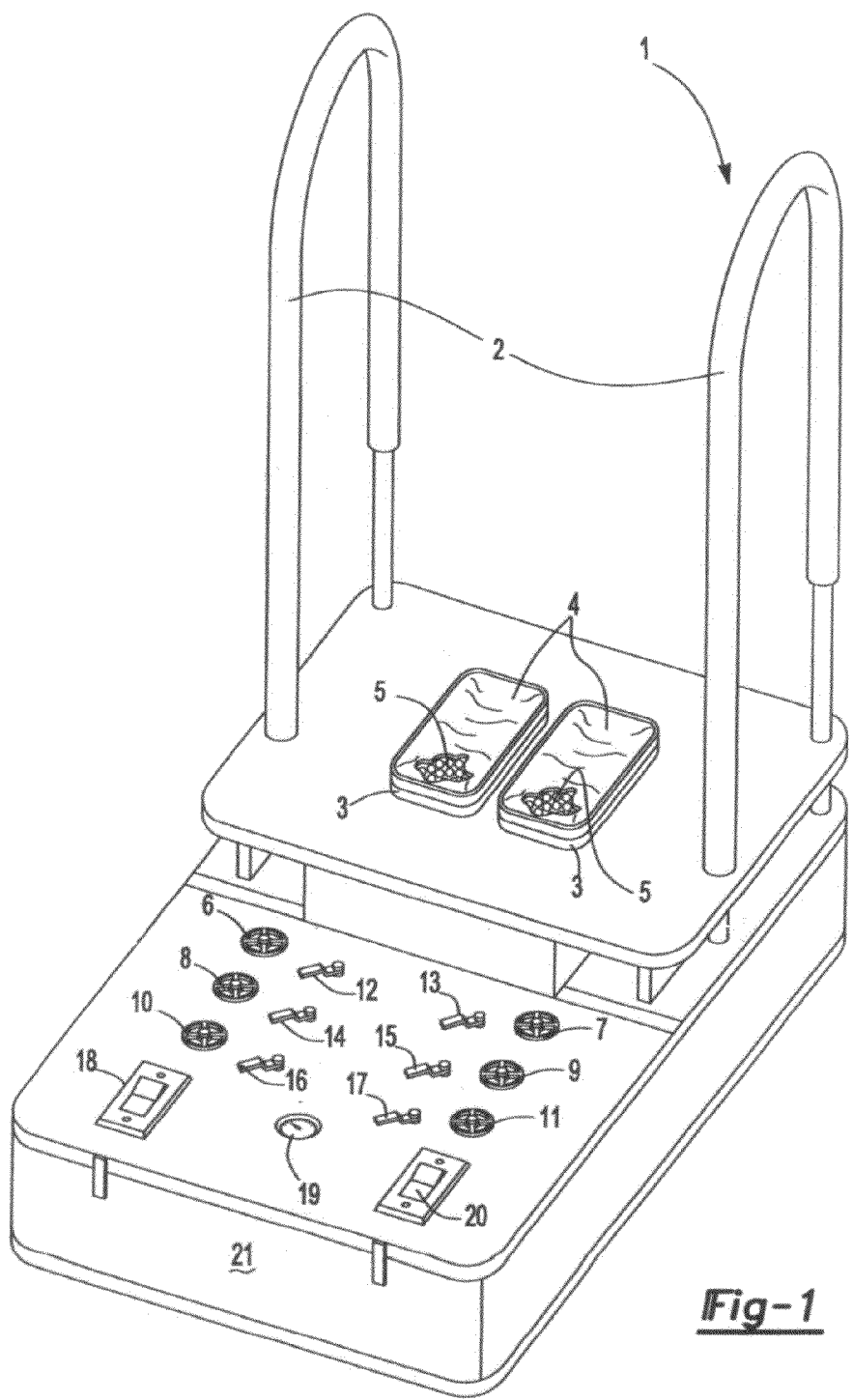
FIG. 1 shows a MIFA Impression Forming Stand for positioning and supporting the legs and feet during impression forming with the MIFA process. The MIFA (Molding Impression Fabrication Apparatus) as shown in FIG. 1 comprises: A MIFA Impression forming Stand (1) with vertical support arms (2); Elastic Membranes (4) Bladder Trays R/H (3) and L/H (3); Cut-outs Showing Glass Beads (Spheres)—(5); R/H Foot Tray Modification Valve (6); L/H Foot Tray Modification Valve (7); R/H Posterior Shell Modification Valve (8); L/H Posterior Shell Modification Valve (9); R/H Anterior Shell Modification Valve (10); L/H Anterior Modification Valve (11); R/H Foot Tray Valve Shut-off (12); L/H Foot Tray Shut-off Valve (13); R/H Posterior Shell Valve Shut-off (14); L/H Posterior Shell Valve Shut-off (15); R/H Anterior Shell Valve Shut-off (16); L/H Anterior Shell Valve Shut-off (17); Vibration On/Off Switch (18); Vacuum Gauge (19); Vacuum Pump On/Off Switch (20); and Operating Component Cabinet (21).
Figure 2:
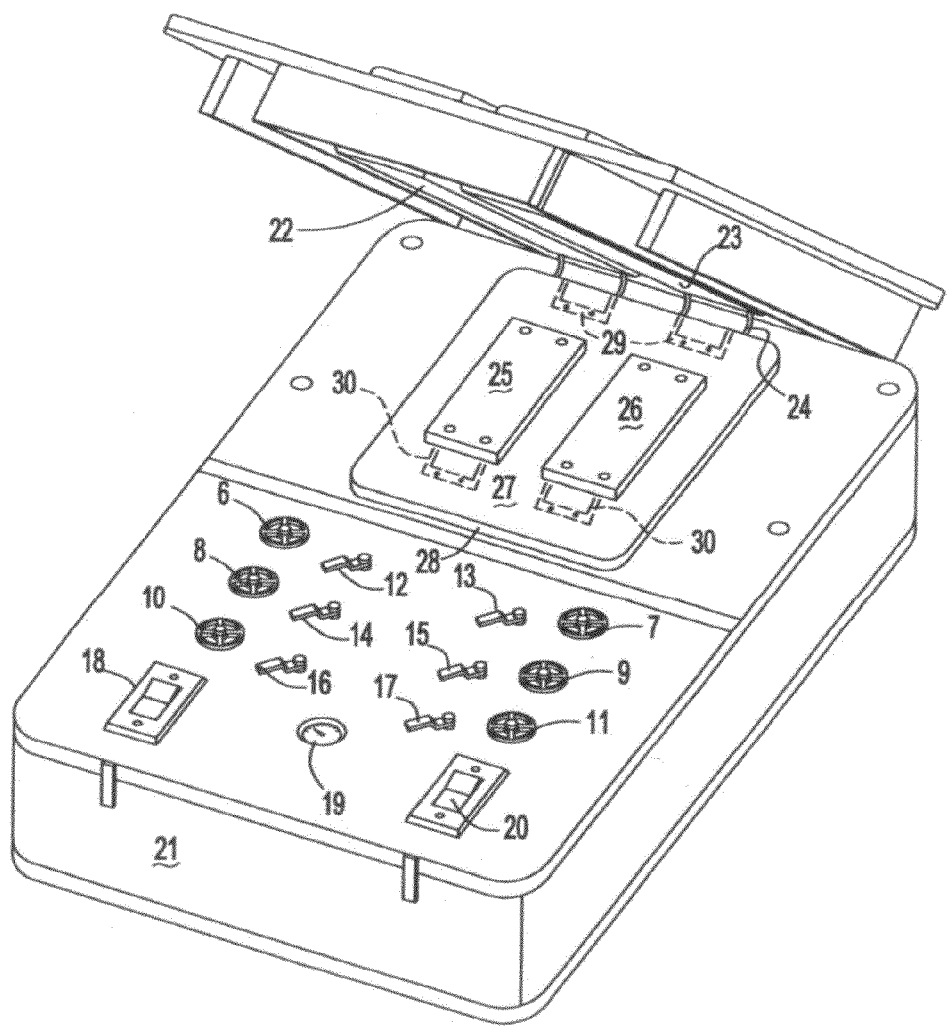
FIG. 2 shows a right foot tray bottom (22); left foot tray bottom (23); vacuum hoses (24); polyurethane foam layer (28); Right Foot Tray Holder (25); Left Foot Tray Holder (26): Vibration Board (27); Posterior Vibration Connectors (29); Anterior Vibration Connectors (30); and Operating Component Cabinet (21). Additional MIFA Operation Components comprise: the Impression Forming Stand (1), and the Hinged Base Cabinet (21) for operation of the MIFA process, that further includes: a Vacuum Reservoir Tank, a Vibration Motor Rest (polyurethane foam on blocks), a Vibration Motor (with the similar excitation frequency as a power vibrating sander, and a Vacuum Pump.
Figure 3:
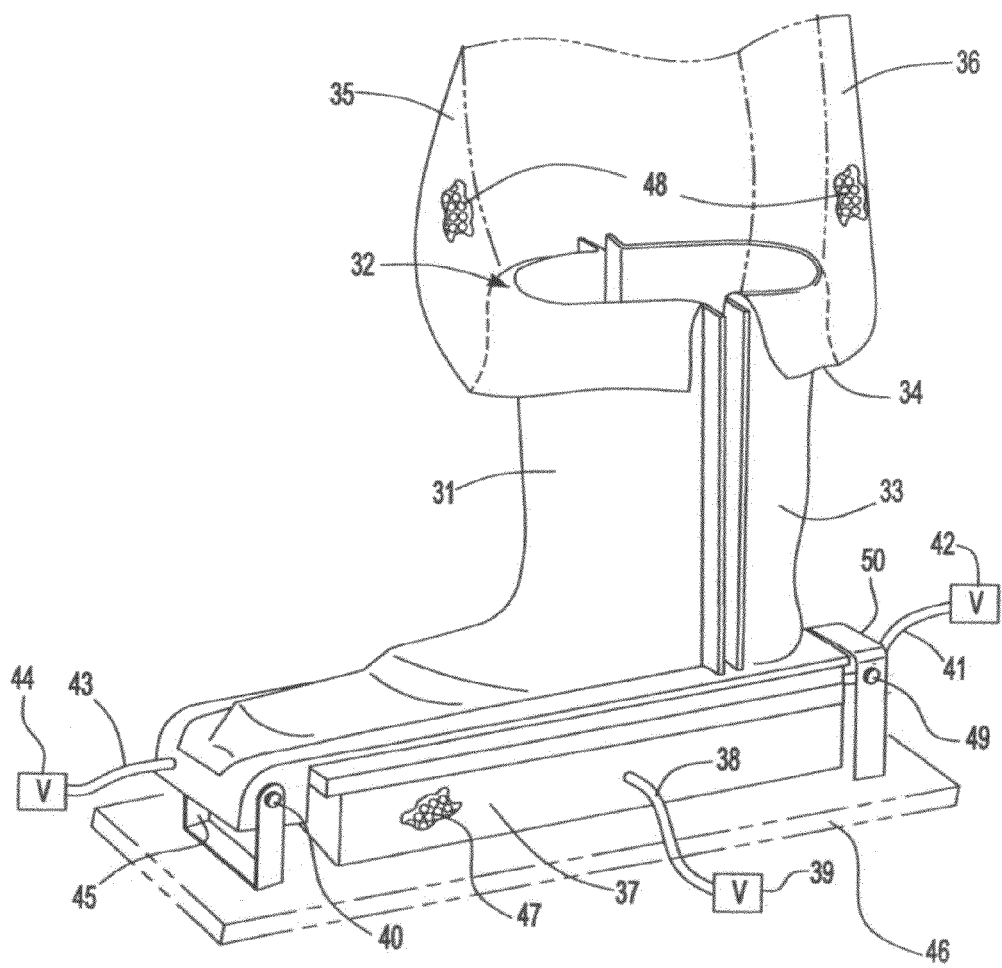
FIG. 3 shows the posterior and anterior shells for positioning the legs during the MIFA impression forming process comprising: Anterior Front Shell (31); Anterior Front Shell Bladder (32); Posterior Back Shell (33); Posterior Back Shell Bladder (34); Anterior Shell Reservoir (35); Posterior Shell Reservoir (36); Shell Reservoir Cut-outs Showing Glass Beads (Spheres) (48); Foot Tray with Bladder (37); Foot Tray Bladder Cut-out Showing Glass Beads (47); Foot Tray Vacuum Hose (38) and Foot Tray Bladder Release Valve (39); Anterior Removable Attachment Bracket (40); Posterior Removal Attachment Bracket (49); Posterior Shell Vacuum Hose (41) and Posterior Bladder Release Valve (42); Anterior Shell Vacuum Hose (43) and Anterior Bladder Release Valve (44); Anterior Vibration Connection (45); Posterior Vibration Connector (50); and Vibration Board (46).

MIFA (Molding Impression Fabrication Apparatus) and enabling process as described in the prior Summary of the Invention, and in The Brief Description of the Drawings, comprises the process steps of: placing the patient in a weight bearing position; or semi-weight bearing position onto the foot tray with bladder; then have the patient assume a subtalar neutral position or corrected alignment, or desired position; then turn on the vibration excitation frequency; and whereby the bladder will then encompass the planter surface medial and lateral walls of the foot and calcaneus, keeping the bladder distal to the malleoli.

Once the corrected position and depth is achieved, then the vibration is shut off, and the vacuum is turned on; then the patient is removed from the impression, and the patient's impression is evaluated. If any modification changes need to be made to the impression, including boney prominences, sores, arthritic areas etc. including intrinsic posting (i.e. changes in the biomechanical ground reaction forces); then the modification valves are opened to relieve some vacuum from the bladders, thus making the bladder impressions malleable for change/modifications. Once modifications are addressed to the practitioner's satisfaction, the valve is closed and the impression will re-assume the solid form or hardening. We then have the first foot impression.

The above MIFA process is repeated for the second foot, as well as other impressions of the leg, arm, or other torso appendages, as required. As with the leg below the knee, the patient is then placed back into their negative foot tray impressions in the bladders; and the anterior shell reservoir bladder, which connects to the vibration board and vacuum, is placed against the patient's anterior leg, encompassing the dorsum of the foot, ankle, and leg going posterior to the mid-sagital line. When the practitioner has the patient positioned to the satisfaction of alignment, etc., the vibration is turned on, continuing the flow of beads into the bladder, filling all cavities between the shell and appendage, thus providing the correct volume within the bladder and the appendage, and forming an exact contour of the appendage. Then the vibration is turned off, and the vacuum is turned on.

Now we have the anterior shell bladder reservoir, and the posterior shell bladder reservoir, which are joined together to encompass the entire leg below the knee. The posterior shell bladder reservoir will meet the anterior shell bladder reservoir, to complete a total circumferential impression of the lower leg. The corresponding vibration and vacuum valves are then used in a like manner, as in the anterior shell bladder. The beads, responsive to this vibration, then assume the surface contours of the patient's leg below the knee. Then both the anterior and posterior units are separated and evaluated by the practitioner, to determine if he chooses to add any changes/modifications to the anterior/posterior impressions.

If modifications/changes are required, then the practitioner will use the modification valves to soften the impressions making it malleable for required modification changes. Once the modifications are completed, then the corresponding valves are closed. Once the valves are closed, the impressions will immediately harden again. Both anterior and posterior valves are required. Each posterior and anterior segment has its own modification and vacuum valves.

Once we have a modified negative impression of the patient we have several options; i.e. make a plaster impression; make CAD/CAM scans; and direct forming (i.e. bio-foam boxes, when you form low temperature plastics between patient and negative impressions).

What is claimed is:
1. A MIFA (Molding Impression Fabrication Apparatus) for providing an orthotic casting impression of a patient's body part with a corrected alignment, comprising:
an impression forming stand having a vertical top portion with vertical support arms, and a mid-foot bed portion, disposed and resting on a bottom base box portion, and wherein the stand rests on a floor supporting surface;
said bottom base box portion further includes a top planar surface portion, side portions, and a bottom portion resting on the stand supporting surface;
left and right foot trays further containing left and right hand bladders, at the mid-foot bed portion;
said bladders further include attachment reservoirs for the disbursement of glass spherical beads with air passage in all directions between the beads;
a vibration board for vibration transmission to the beads, allowing said beads to move freely within the bladders forming a detailed image contour of the body, part against the bladders;
a vacuum pump and vacuum switches providing a vacuum to said bladders, for forming an impression after said vibration is shut off to the beads, forming a hardened rigid impression of the patient's body part;

modification valves are provided to relieve vacuum from the bladders thus making the bladder impressions of said patient's body part malleable for change modifications; and an operating component hinged base cabinet is provided at the bottom base portion of said MIFA impression forming stand, further including a vacuum reservoir tank, vibration motor, vacuum pump, and air relief valves for each bladder.

2. The MIFA impression forming apparatus as recited in claim 1, wherein the mid-foot bed portion of said MIFA impression forming stand is hinged, and further disposed between two planar surface boards, thus enabling the practitioner to swing the left and right foot trays up above the planar surface of the left and right foot tray bladders, to reveal and access the vibration board, polyurethane foam layer, and vacuum hoses during operation and maintenance; and wherein the mid-foot bed portion rests on the bottom base box portion, of said impression forming stand.

3. The MIFA impression forming apparatus as recited in claim 1, wherein the top planar surface portion of said base box portion of said casting stand is disposed to receive vibration on/off switches, vacuum on/off valves, vacuum pump on/off switches, left and right vacuum on/off valves, and left and right hand modification valves.

4. The MIFA impression forming apparatus as recited in claim 1, wherein the bladders, and said bladder reservoirs, with said spherical beads are contained in anterior, posterior, and foot tray boot like shells, that are hinged and disposed to receive, and make an impression of the patient's leg.

5. The MIFA impression forming apparatus as recited in claim 1, wherein the bladders, and bladder reservoirs, with spherical beads are contained in anterior, posterior, and leg impression forming shells.

6. The MIFA impression forming apparatus as recited in claim 1, wherein the bladders, and bladder reservoirs, with spherical beads are contained in impression forming shells disposed to receive a patient's arm to make an arm orthosis impression.

7. The MIFA impression forming apparatus as recited in claim 1, wherein the bladders, bladder reservoirs, with spherical beads are contained in anterior and posterior total body shells, enabling the operator to obtain an accurate total body orthosis impression of the patient's torso.

8. The MIFA impression forming apparatus as recited in claims 4, 5, 6, or 7, wherein the spherical beads are subjected to a vibration transmission within the bladders, shell, and tray reservoirs, and allowed to move freely to form a detailed contour or image of the body part against the bladder.

9. The MIFA impression forming apparatus as recited in claim 1, wherein modification valves are provided to relieve vacuum from the bladders thus making the bladder impressions more malleable for change/modifications so as to obtain the optimum orthosis mold.

10. The MIFA impression forming apparatus as recited in claim 1, is used in conjunction with a CAD/CAM system feedback control loop scanning device to optimize the change/modification mold provided by the modification valves, wherein the positive corrected impression can be directly checked against the negative impression, with CAD/CAM digital scanned data.

11. The MIFA impression apparatus as recited in claim 1, wherein all the foot trays and shells are removable from said apparatus with quick release valve connectors.

12. The MIFA impression apparatus as recited in claim 1, wherein foot tray bladder, posterior bladder, and anterior bladder quick release air valves are provided to remove air from the bladders.

13. A method of obtaining a MIFA impression forming orthosis comprising the process steps of:
   a) providing a bladder covering the anatomical portion to be molded in a semi-rigid shell;
   b) disposing glass beads in an attachment reservoir of said bladder;
   c) introducing a vibration transmission to the beads to allow them to move freely within the bladder and the reservoir;
   d) forming a detailed contour or image of the body part against the bladder from the proper disbursement of the beads between the body part and the shell;
   e) introducing a vacuum after the vibration is turned off on the spherical beads forming the patient's negative impression to harden;
   f) providing modifications and relief changes in the impression, by opening a modification valve to relieve vacuum from the bladder, thus making the bladder impression malleable for change/modifications; and
   g) pouring and making a positive plaster impression of the negative mold for the optimum and corrected mold for fabricating an orthosis.

\* \* \* \* \*